US006937903B2

(12) United States Patent
Schuler et al.

(10) Patent No.: US 6,937,903 B2
(45) Date of Patent: *Aug. 30, 2005

(54) RESPIRATORY CONTROL BY MEANS OF NEURO-ELECTRICAL CODED SIGNALS

(75) Inventors: Eleanor Schuler, Rio Rancho, NM (US); Claude K. Lee, Reno, NV (US)

(73) Assignee: Science Medicus, Inc., Albuquerque, NM (US)

( * ) Notice: Subject to any disclaimer, the term of this patent is extended or adjusted under 35 U.S.C. 154(b) by 1 day.

This patent is subject to a terminal disclaimer.

(21) Appl. No.: 10/847,738

(22) Filed: May 17, 2004

(65) Prior Publication Data

US 2004/0230251 A1 Nov. 18, 2004

Related U.S. Application Data

(60) Provisional application No. 60/471,104, filed on May 16, 2003.

(51) Int. Cl.[7] .................................................. A61N 1/18
(52) U.S. Cl. ............................. 607/42; 601/15; 607/68
(58) Field of Search ........................... 607/42, 73, 68, 607/62, 48, 76; 601/15, 2

(56) References Cited

U.S. PATENT DOCUMENTS

| 4,832,033 A | * | 5/1989 | Maher et al. ................. 607/48 |
| 6,633,779 B1 | * | 10/2003 | Schuler ........................ 607/42 |
| 6,651,652 B1 | * | 11/2003 | Ward ...................... 128/200.24 |

* cited by examiner

Primary Examiner—Jeffrey R. Jastrzab
Assistant Examiner—Alyssa M. Alter
(74) Attorney, Agent, or Firm—Francis Law Group

(57) ABSTRACT

A method and device for respiratory control. The method comprises selecting neuro-electrical coded signals from a storage area that are representative of body organ function. The selected neuro-electrical coded signals are then transmitted to a treatment member, which is in direct contact with the body, and which then broadcasts the neuro-electrical coded signals to a specific body respiration nerve or organ to modulate the body organ functioning. A control module is provided for transmission to the treatment member. The control module contains the neuro-electrical coded signals which are selected and transmitted to the treatment member, and computer storage can be provided for greater storage capacity and manipulation of the neuro-electrical coded signals.

14 Claims, 2 Drawing Sheets

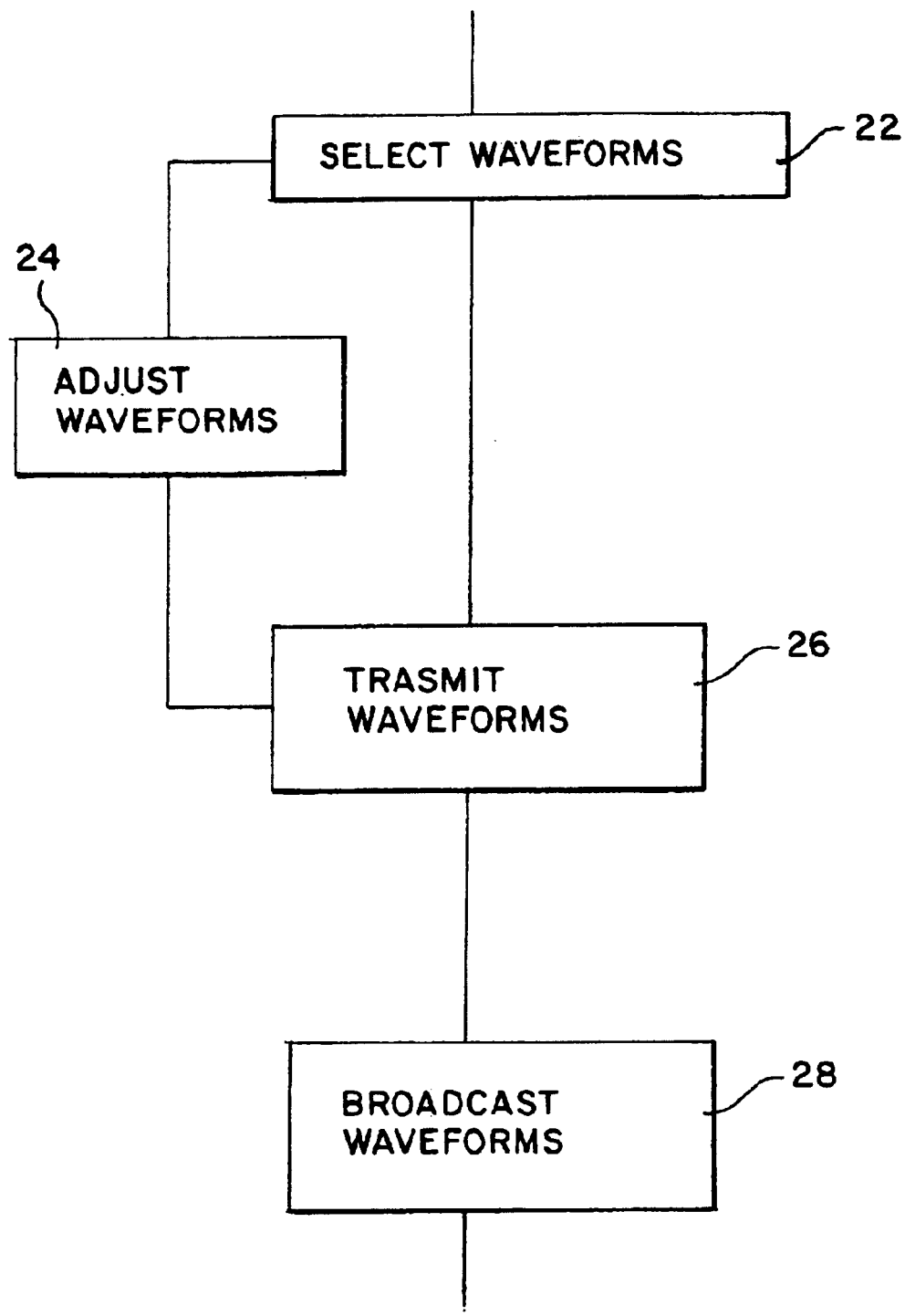

RESPIRATORY CONTROL BY MEANS OF NEURO-ELECTRICAL CODED SIGNALS

RELATED APPLICATION

This is the non-provisional filing of application Ser. No. 60/471,104, filed on May 16, 2003, entitled "Respiratory Control by Means of Neuro-Electrical Coded Signals."

BACKGROUND OF THE INVENTION

This invention relates to a method for respiratory control by means of neuro-electrical coded signals.

Respiration is a key component of human life. The lungs remove oxygen from air for transport via the blood stream to the entire body. Entrance of air to the lungs must travel through bronchial tubes which can open or close in response to many stimuli. For example, once bronchi constrict and plug with mucus in response to inhaled allergens, as occurs in asthma, the quantity of air is greatly impaired and oxygen starvation begins. Continual evolution of a constricted and mucus filled bronchial tree is always life threatening. This invention offers a way to lower mucus secretion rates and cause dilation of the bronchial tree.

The airways of the lungs begin at the trachea (wind pipe) and move downward where the trachea bifurcates (divides) into the right and left bronchi. As each enters its respective lung it turns into lobar then segmented bronchi. It should be noted that the trachea and the major bronchi are supported by C-shaped cartilaginous hoops. The hoops help maintain the shape of the larger bronchial tubal structures. The "C" is open posteriorly where the bronchial tube is closed by muscle. Bronchial muscle plays an important part in opening and closing bronchial tubes. The evolvement of the bronchial process goes through about 20 reductions in diameter as it continues down to the terminal bronchioles, which are the smallest airways without alveoli.

Bronchi are muscular and can change their lumen (inside) diameter in response to certain stimuli including input from the brain. The terminal bronchi divide into respiratory bronchioles which now have occasional alveoli budding from their walls. Finally, the bronchioles lead to the alveolar ducts that are fully lined with alveoli.

Alveoli, or an alveolus, are tiny sac-like structures where the exchange of oxygen and carbon dioxide occurs. These are commonly called air-sacs. The alveolated region of the lung is known as the respiratory zone. The air filled sacs are lined by flat pneumocytes which secrete a low surface tension surfactant to keep the alveoli patent (open). Only a very thin barrier exists between the pulmonary blood supply and the inspired air where a rapid gas exchange occurs.

The bronchi and air-sacs operate within both lungs. The right lung has 3 lobes and the left lung has 2 lobes. This respiratory system has essentially 2 functions, which are ventilation and gas exchange. The mechanics of breathing consist of inspiration (breathing in) and expiration (breathing out). The driving force for ventilation is the pressure difference between the atmosphere and the intra pulmonic pressure in the alveoli. There are some 300 million alveoli operating in both lungs.

The alveoli are of 2 types. Type I has the shape of a fried egg but with long cytoplasmic (all of the operational contents of a cell except the nucleus) extensions spreading out thinly over the alveolar walls. Type II alveoli are more compact and excrete surfactant by exocytosis. Destruction or injury to type II alveoli leads to a surfactant deficiency which in turn lowers compliance and directly results in pulmonary edema among other complications. As air passes from outside the body into the lungs it is progressively moisturized and when it arrives at the alveoli air is fully saturated with moisture.

The blood supply for the alveoli is provided by an enmeshed dense network of pulmonary capillaries. Carbon dioxide diffuses from the blood into the alveoli where it escapes into the lung spaces while oxygen from the alveoli travels directly into the blood transport over the body.

Many nerves and muscles play a part in efficient breathing. The most important muscle devoted to breathing is the diaphragm. With normal tidal breathing the diaphragm moves about 1 cm, but in forced breathing the diaphragm can move up to 10 cm. The left and right phrenic nerves activate diaphragm movement. The diaphragm is a sheet-shaped muscle which separates the thoriac cavity from the abdominal cavity. Its contraction and relaxation account for a 75% volume change in the thorax during normal quiet breathing. Contracting of the diaphragm as a result of electrical brain signals occurs during inspiration. Expiration happens when the diaphragm relaxes and recoils to its resting position. Indirect influences on inspiration are exerted when the thorax enlarges because of contraction of the scalene and external intercostal muscles. Interestingly, either the diaphragm or the external intercostal muscles can maintain adequate chest cavity movement to maintain adequate ventilation at rest. But during full exertion they are all needed to participate in heavy and rapid breathing. All movements are controlled by electrical nerve signals or waveforms traveling from the brain to the respective muscle structures previously described.

The afferent and efferent nerves travel together and are assisted by afferent lower intercostal nerves in providing information and signals to control the diaphragm in its breathing role. The fourth cranial nerve (trochlear) provides input in operating the diaphragm via the phrenic nerve(s) with assistance from both the third cranial nerve (oculomotor) and the fifth nerve (trigeminal). During normal breathing the expiration process is largely automatic since the lung and chest wall recoil to their normal equilibrium positions. But with inspiration a number of thoriac muscles play a role to expand the lungs and draw in the air. The inspiration process is accomplished by increasing the volume of the chest cavity as the diaphragm muscle contracts.

Control of normal breathing is largely under the direction of the brain stem. However, part of the limbic system of the brain and hypothalamus have the ability to accelerate the pattern of breathing in times of fear or rage. There are chemoreceptors involved in minute-by-minute breathing control which are located in the vicinity of the exit points of the ninth cranial (glossopharyngeal) and tenth cranial (vagus) nerves of the medulla oblongata, near the medulla oblongata's ventral surface.

Additional afferent nerves that arise from sensors that measure blood chemistry act as a sort of status report on how oxygenation is proceeding. The most important are peripheral chemoreceptors located at the bifurcation of the carotid arteries in the neck and also at the heart region in the aorta, above and below the heart's aortic arch. Afferent innervation brings rapid information to the brain to be computed prior to instructing efferent nerves on how to control breathing. The chemoreceptors described are directly involved in how the vagus nerve responds with its own instructional waveform to the bronchi, lungs and heart, all of which are concerned with breathing and blood circulation. There are also mechanoreceptors which measure pressure, vibration and movement that have afferent input to the respiratory and cardiac system. There are also stretch receptors in lungs that tell the brain how the lung is cycling. Also thermal receptors respond to the brain on heat or cold status of the various components. Other inputs to the medulla and the pons area of the brain stem include proprioceptors (a kind of deep sensing related to muscle and tendons) which coordinate muscular activity with respiration. Then there are baroreceptors which send afferent signals to the medullary center as well as to the cardioinhibitory in the medulla to help match pulse rate, blood pressure and respiratory rate in a fine tuning effort necessary for body homeostasis.

The central nervous system (brain) nerves involved in breathing are the second, third, fourth, fifth, eighth, ninth, and the important tenth (vagus) cranial nerves. The first cranial nerve supplies olfactory information and the second and third nerves are related to inputs from the eyes as afferent sensors which integrate what the body is perceiving from outside and demands faster or slower breathing rates or even holding ones breath. The eighth cranial nerve provides auditory afferent input. The various afferent sensory neurofibers provide information as to how the body should be breathing in response to events outside the body proper.

An important, even the key, respiratory control, is activated by the vagus nerve and its preganglionic nerve fibers which synapse in ganglia embedded in the bronchi that are also enervated with sympathetic and parasympathetic activity. The sympathetic nerve division can have no effect on bronchi or it can dilate the lumen (bore) to allow more air to enter the respiratory process, which is helpful to asthma patients, while the parasympathetic process offers the opposite effect and is able to constrict the bronchi and increase secretions, which is harmful to asthma patients.

SUMMARY OF THE INVENTION

The invention provides a method for controlling respiration. Stored neuro-electrical coded signals that are generated and carried in the body are selected from a storage area. The selected waveforms are then transmitted to a treatment member which is in direct contact with the body. The treatment member then broadcasts the selected neuro-electrical coded signals to an organ in the body.

The neuro-electrical coded signals may be selected from a storage area in a computer, such as a scientific computer. The process of transmitting the selected neuro-electrical coded signals can either be done remotely or with the treatment member connected to a control module. The transmission may be seismic, electronic, or via any other suitable method.

The invention further provides an apparatus for controlling respiration. The apparatus includes a source of collected neuro-electrical coded signals that are indicative of body organ functioning, a treatment member in direct contact with the body, means for transmitting collected waveforms to the treatment member, and means for broadcasting the collected neuro-electrical coded signals from the treatment member to a body organ.

The transmitting means may include a digital to analog converter. The source of collected waveforms preferably comprises a computer which has the collected waveforms stored in digital format. The computer may include separate storage areas for collected neuro-electrical coded signals of different categories.

The treatment member may be comprised of an antenna or an electrode, or any other means of broadcasting one or more neuro-electrical coded signals directly to the body.

BRIEF DESCRIPTION OF THE DRAWINGS

The invention is described in greater detail in the following description of examples embodying the best mode of the invention, taken in conjunction with the drawing figures, in which:

FIG. 3 is a flow chart of the method according to the invention.

DESCRIPTION OF EXAMPLES EMBODYING THE BEST MODE OF THE INVENTION

Figure 1:
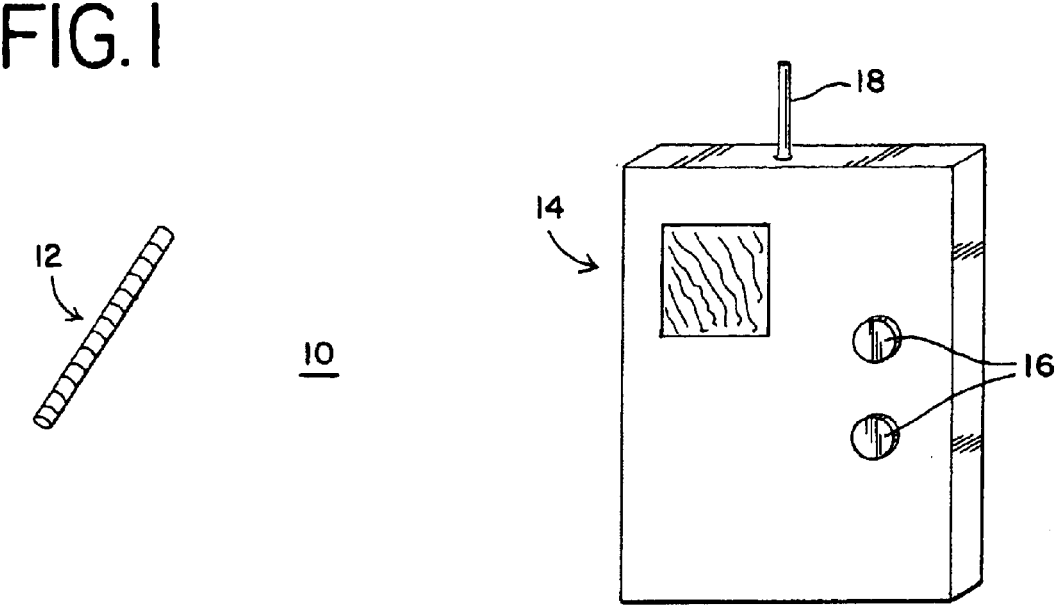
FIG. 1 is a schematic diagram of one form of apparatus for practicing the method according to the invention.

For the purpose of promoting an understanding of the principles of the invention, references will be made to the embodiments illustrated in the drawings. It will, nevertheless, be understood that no limitation of the scope of the invention is thereby intended, such alterations and further modifications in the illustrated device, and such further applications of the principles of the invention illustrated herein being contemplated as would normally occur to the one skilled in the art to which the invention relates.

Controlling respiration my requires sending electrical waveforms into one or more nerves, including up to five nerves simultaneously to control respiration rates and depth of inhalation. The correction of asthma or other breathing impairment or disease involves the rhythmic operation of the diaphragm and/or the intercostal muscles to inspire and expire air for the extraction of oxygen and the dumping of waste gaseous compounds such as carbon dioxide.

The opening up (dilation) of the bronchial tubular network allows for more air volume to be exchanged and processed for its oxygen content within the lungs. The dilation process can be electrically controlled by coded waveform signals. The bronchi can also be closed down to restrict air volume passage into the lungs. A balance of controlling nerves for dilation and/or constriction can be done via the invention.

Mucus production if excessive can form mucoid plugs that restrict air volume flow throughout the bronchi. No mucus is produced by the lung except in the lumen of the bronchi and also in the trachea. This mucus production can be increased or decreased by electrical coded signals. Signals can balance the quality and quantity of the mucus.

All coded signals operate at less than 1 volt, naturally. Applied voltage may be up to 20 volts according to the invention to allow for voltage loss during the transmission or conduction of the required coded signals. Current should always be less than 2 amp output for the invention. Direct conduction into the nerves via electrodes connected directly to such nerves will likely have outputs of less than 3 volts and current of less than one tenth of an amp.

The present invention is able to control respiration rates and strength along with bronchial tube dilation and mucinous action in the bronchi by controlling the waveforms transmitted into the body. Such ability to open bronchi will be useful for treatment of acute bronchitis or smoke inhalation injuries in the emergency room. Chronic airway obstructive disorders such as emphysema can also be addressed.

Acute fire or chemical inhalation injury treatment can be enhanced while using mechanical respiration support. Injury mediated mucus secretions also lead to obstruction of the airways and are refractory to urgent treatment, posing a life-threatening risk. Edema (swelling) inside the trachea or bronchial tubes tends to limit bore size and cause oxygen starvation. The ability to open bore size is essential or at least desirable during treatment.

The effort of breathing in patients with pneumonia may be eased by modulated activation of the phrenic nerve by the invention. Treatment of numerous other life threatening conditions revolve around a well functioning respiratory system. Therefore, the invention provides the physician with a method to open bronchi and fine tune the breathing rate to improve oxygenation of patients. This electronic treatment method encompasses the broadcasting of activating or suppressing waveforms onto selected nerves to improve respiration. Such treatments would be augmented by oxygen administration and the use of respiratory medications which are presently available.

The invention encompasses both a device and a method for respiratory control by means of neuro-electrical coded signals. One form of a device 10 for respiratory control, as shown in FIG. 1, is comprised of at least one treatment member 12, and a control module 14. The treatment member 12 is in direct contact with a body and receives a neuro-electrical coded signal from the control module 14. The treatment member 12 may be an electrode, antenna, a seismic transducer, or any other suitable form of conduction attachment for broadcasting respiratory signals that regulate or operate breathing function in human or animals. The treatment member 12 may be attached to appropriate nerves or respiratory organ(s) in a surgical process. Such surgery may be accomplished with "key-hole" entrance in a thoriac-stereo-scope procedure. If necessary a more expansive thoracotomy approach may be required for more proper placement of the treatment member 12. Furthermore, if necessary, the treatment member 12 may be inserted into a body cavity such as the nose or mouth and may pierce the mucinous or other membranes so as to arrive in close proximity of the medulla oblongata and/or pons. Neuro-electrical coded signals known to modulate respiratory function may then be sent into nerves that are in close proximity with the brain stem.

The control module 14 is comprised of at least one control 16, and an antenna 18. The control 16 allows the device to regulate the signal transmission into the body. As shown in FIG. 1, the control module 14 and treatment member 12 can be entirely separate elements allowing the device 10 to be operated remotely. The control module 14 can be unique, or can be any conventional device which can provide neuro-electrical coded signals for transmission to the treatment member 12.

Figure 2:
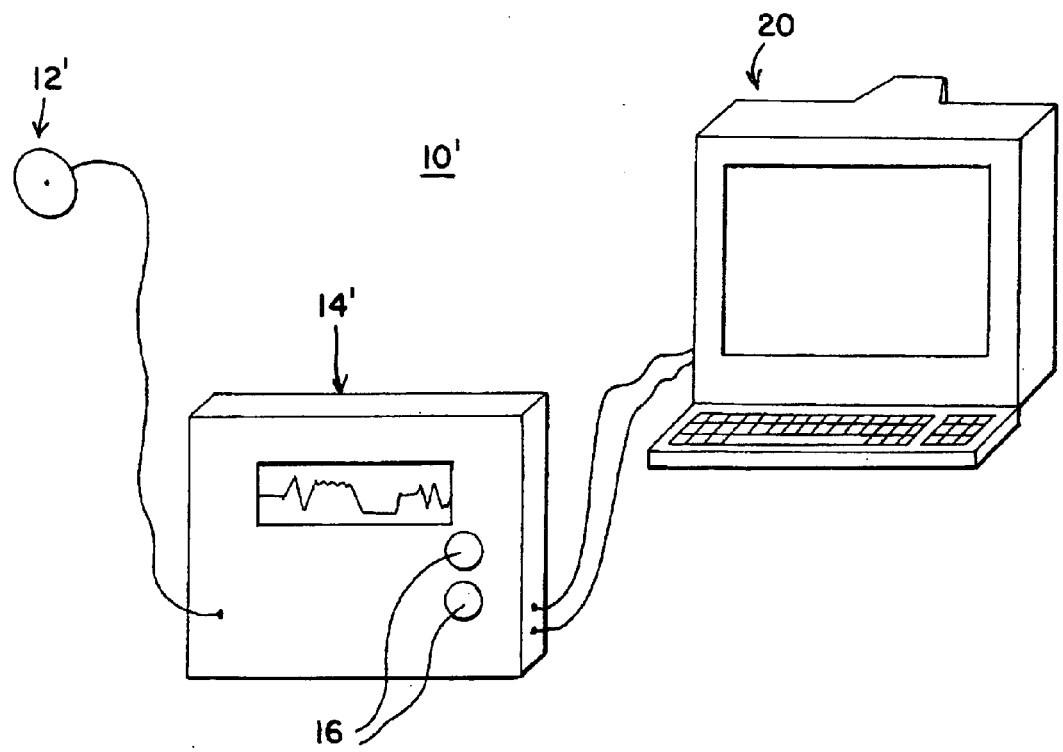
FIG. 2 is a schematic diagram of another form of apparatus for practicing the method according to the invention.

In an alternate embodiment of the device 10, as shown in FIG. 2, the control module 14' and treatment member 12' are connected. Similar members retain the same reference numerals in this figure. Additionally, FIG. 2 further shows another embodiment of the device 10' as being connected to a computer 20, which provides greater capacity to store the neuro-electrical coded signals. The output voltage and amperage provided by the device 10' during treatment shall not exceed 20 volts nor 2 amps for each signal.

The computer 20 is used to store the unique neuro-electrical coded signals, which are complex and unique to each organ and function of the organ. It is a neuro-electrical coded signal(s) selected from the stored library of waveforms in the computer 20 which is transmitted to the control module 14' and used for treatment of a patient. The waveform signals, and their creation, are described in greater detail in U.S. patent application Ser. No. 10/000,005, filed Nov. 20, 2001, and entitled "Device and Method to Record, Store, and Broadcast Specific Brain Waveforms to Modulate Body Organ Functioning," the disclosure of which is incorporated herein by reference.

The invention further includes a method, as shown in FIG. 3, for using the device 10, 10' for respiratory control. The method begins at step 22 by selecting one or more stored neuro-electrical coded signals from a menu of cataloged neuro-electrical coded signals. The neuro-electrical coded signals selected activate, deactivate, or adjust the respiratory system. Such neuro-electrical coded signals are similar to those naturally produced by the brain stem structures for balancing and controlling respiratory processes. Once selected, the neuro-electrical coded signals may be adjusted, in step 24, to perform a particular function in the body. Alternatively, if it is decided that the neuro-electrical coded signals do not need to be adjusted, step 24 is skipped and the process proceeds directly with step 26. At step 26, the neuro-electrical coded signal is transmitted to the treatment member 12, 12' of the device 10, 10'.

Upon receipt of the neuro-electrical coded signals, the treatment member 12, 12' broadcasts the neuro-electrical coded signals to the appropriate respiratory organ or nerve location, as shown in step 28. The device 10, 10' utilizes appropriate neuro-electrical coded signals to adjust or modulate respiratory action via conduction or broadcast of electrical signals into selected nerves. It is believed that target organs can only uniquely "hear" their own individual neuro-electrical coded. As a result, the body is not in danger of having one organ perform the function of another organ simply because the first organ received the second organ's neuro-electrical coded.

In one embodiment of the invention, the process of broadcasting by the treatment member 12, 12' is accomplished by direct conduction or transmission through unbroken skin in a selected appropriate zone on the neck, head, or thorax. Such zone will approximate a position close to the nerve or nerve plexus onto which the signal is to be imposed. The treatment member 12, 12' is brought into contact with the skin in a selected target area that allows for the transport of the signal to the target nerve.

In an alternate embodiment of the invention, the process of broadcasting the neuro-electrical coded signal is accomplished by direct conduction via attachment of an electrode to the receiving nerve or nerve plexus. This requires a surgical intervention as required to physically attach the electrode to the selected target nerve.

In yet another embodiment of the invention, the process of broadcasting is accomplished by transposing the neuro-electrical coded signal into a seismic form where it is sent into a region of the head, neck, or thorax in a manner that allows the appropriate "nerve" to receive and to obey the coded instructions of such seismic signal. The treatment member 12, 12' is pressed against the unbroken skin surface using an electrode conductive gel or paste medium to aid conductivity.

Various features of the invention have been particularly shown and described in connection with the illustrated embodiments of the invention. However, it must be understood that these particular products, and their method of manufacture, do not limit but merely illustrate, and that the invention is to be given its fullest interpretation within the terms of the appended claims.

We claim:

1. A method for controlling respiration comprising the steps of:

a. selecting from a storage area one or more waveforms generated in the body and carried by neurons in the body;

b. transmitting or conducting the selected waveforms to a treatment member in contact with the body; and c. broadcasting the selected waveforms from the treatment member to an area in the body such that an organ in the body is affected to control respiration.

2. The method according to claim 1, in which step "a" further includes selecting said waveforms from a storage area in a computer.

3. The method according to claim 1, in which step "b" further comprises transmitting the selected waveforms remotely to the treatment member.

4. The method according to claim 1, in which step "b" further comprises seismic transmission of the selected waveforms.

5. An apparatus for controlling respiration, comprising:

a. a source of collected waveforms generated in the body and indicative of body organ functioning;

b. a treatment member adapted to be in direct contact with the body;

c. means for transmitting one or more of the collected waveforms to the treatment member; and d. means for broadcasting the collected waveforms from the treatment member to an area in the body such that a body organ is affected, thereby controlling respiration.

6. The apparatus according to claim 5, in which said transmitting means includes a digital to analog converter.

7. The apparatus according to claim 5, in which said source comprises a computer having collected waveforms stored in digital format.

8. The apparatus according to claim 7, in which said computer includes separate storage areas for collecting waveforms of different respiratory functional categories.

9. The apparatus according to claim 5, in which the treatment member comprises an antenna for broadcasting respiratory signals.

10. The apparatus according to claim 5, in which the treatment member comprises an electrode.

11. A method for controlling respiration comprising the steps of:

a. selecting from a storage area one or more waveforms generated in the body and carried by neurons in the body;

b. transmitting or conducting the selected waveforms to a treatment member in contact with the body; and c. directing the selected waveforms from the treatment member to a point in a body to control respiration.

12. The method according to claim 11, in which step "a" further includes selecting said waveforms from a storage area in a computer.

13. The method according to claim 11, in which step "b" further comprises transmitting the selected waveforms remotely to the treatment member.

14. The method according to claim 11, in which step "b" further comprises seismic transmission of the selected waveforms.

* * * * *